United States Patent [19]

Angell

[11] 4,247,292
[45] Jan. 27, 1981

[54] NATURAL TISSUE HEART VALVE FIXATION PROCESS

[76] Inventor: William W. Angell, 27385 Deer Springs Way, Los Altos Hills, Calif. 94022

[21] Appl. No.: 46,100

[22] Filed: Jun. 6, 1979

[51] Int. Cl.$^3$ .................. A61L 17/00; C14C 3/00; C14C 15/00; A61C 1/22
[52] U.S. Cl. .................................. 8/94.11; 3/1.5; 128/274
[58] Field of Search ...................... 8/94.11; 3/1, 1.5

[56] References Cited

U.S. PATENT DOCUMENTS

| | | | |
|---|---|---|---|
| 3,966,401 | 6/1976 | Hancock et al. | 8/94.11 |
| 3,983,581 | 10/1976 | Angell | 3/1.5 |
| 4,035,849 | 7/1977 | Angell et al. | 8/94.11 |
| 4,050,893 | 9/1977 | Hancock et al. | 8/94.11 |
| 4,090,878 | 5/1978 | Hancock et al. | 69/29 |

OTHER PUBLICATIONS

Broom "Fatigue-Induced Damage in Glutaraldehyde Preserved Heart Valve Tissue" J. Thorack & Card, vol. 76 (2) 202–211.
Biosis Abst., vol. 66, Jul. 15, 1978, 6843 Broom, "The Stress/Strain & Fatigue Behavior of Glutaraldehyde Preserved Heart-Valve Tissue".
*Industrial Gums*, Polysaccharides and their Derivatives, 2nd Ed., by Roy L. Whistler, p. 85.
*Indian Textile Journal* Utilization of Tamarind Seed Pectin in Textile Industries, Part III Potentialities of Pectin in Printing by G. R. Savur, (1956) pp. 309–311 and 33–35 (1955).

*Primary Examiner*—Joseph L. Schofer
*Assistant Examiner*—Herbert J. Lilling
*Attorney, Agent, or Firm*—Thomas E. Ciotti

[57] ABSTRACT

A process for fixing a natural tissue heart valve whereby the valve has improved hydraulic performance is disclosed. The valve is first placed in glutaraldehyde with the valve cusps kept in the closed position by applying hydraulic pressure to the ventricular side of the valve. The valve is then trimmed and fitted to and sutured into a fabric covered plastic stent. An expandable tube is then placed axially within the valve and expanded to force the valve cusps into an open position. The expanded tube-valve-stent assembly is then placed in glutaraldehyde to further fix the valve and predispose the valve cusps to an open position.

11 Claims, 10 Drawing Figures

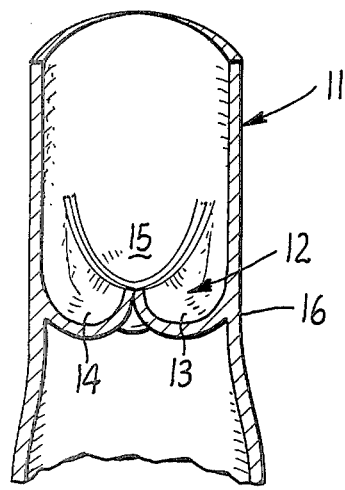
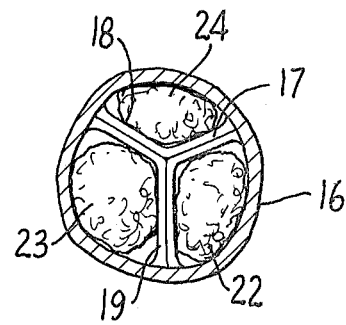
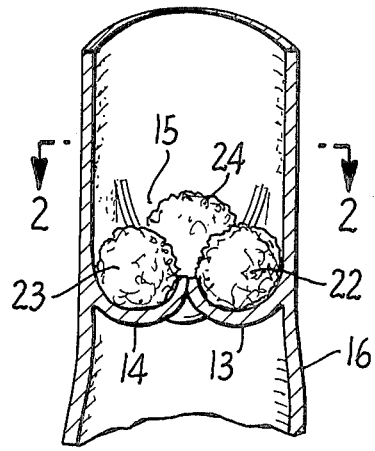
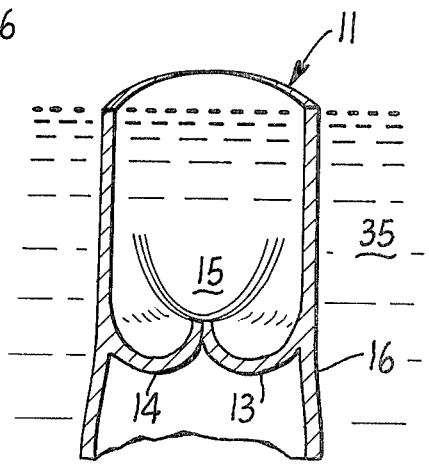
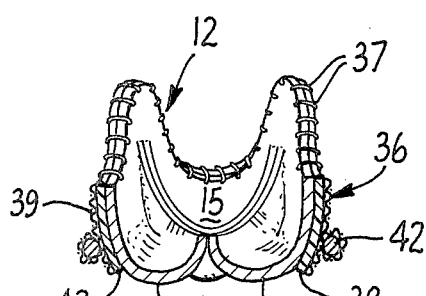
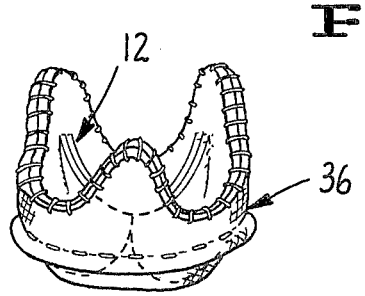
FIG.1A.
FIG.2.
FIG.1B.
FIG.1C.
FIG.1D.
FIG.3.

NATURAL TISSUE HEART VALVE FIXATION PROCESS

BACKGROUND OF THE INVENTION

1. Field of the Invention

This invention relates to a process for fixing (tanning) natural tissue heart valve prostheses.

2. Description of the Prior Art

It is known that the tensile properties and antigenic reaction of a natural tissue heart valve prosthesis may be improved by fixing the valve before it is implanted. Glutaraldehyde is commonly used as a fixing agent.

Commonly owned U.S. Pat. Nos. 3,983,581 and 4,035,849 describe a fixing procedure in which porcine valves are fixed in glutaraldehyde with the valve cusps held in a closed position by applying hydraulic pressure to the ventricular side of the valve.

Thompson, F J and Barratt-Boyes, B G, "The Glutaraldehyde-treated Heterograft Valve", *Journal of Thoracic and Cardiovascular Surgery*, Vol 74, No 2, pp 317–321, August 1977, report in vitro tests comparing heterograft valves that were apparently fixed in glutaraldehyde with the cusps closed under "physiological pressure" with antibiotic-treated homograft valves. The heterograft valves were reported to remain closed at zero pressure across the valve and to not fully open until the flow rate (Piper's solution at 37° C.) through the valve was greater than 10 liters per minute. The article concluded that the cusps of the heterograft valve do not open as freely as those of the homograft valve and that such performance may be responsible for the rather high pressure drop across heterograft valves reported by prior investigators.

The main object of the invention process is to make natural tissue heart valve prostheses whose cusps open more freely. Such valves are characterized by improved in vivo hydraulic performance.

SUMMARY OF THE INVENTION

The invention is an improved two-step process for fixing a natural tissue heart valve prosthesis. The first step involves contacting the valve with a fixing agent with the valve cusps in a closed position for a time sufficient to partially fix the valve such that the configuration and dimensions of the valve are substantially set. In the second step the valve is again contacted with the fixing agent but with the valve cusps in an open position rather than closed. This second step is carried out for a time sufficient to further fix the valve and predispose the valve cusps to an open position.

In a preferred embodiment of the process the valve is placed in a support member, such as a stent, before the second step is carried out. Such placement prevents any substantial radial expansion of the valve during the second step.

BRIEF DESCRIPTION OF THE DRAWINGS

The figures in the drawings depict a valve as it appears during various stages of the invention process. Specifically, in the drawings:

FIG. 1A is a sectional view of an aortic root, including a valve, as taken from a donor;

FIG. 1B is a sectional view of the root of FIG. 1A showing the valve packed into a closed position for initial fixation;

FIG. 1C is a sectional view of the root of FIGS. 1A and 1B stored in saline after the initial fixation;

FIG. 1D is a sectional view of the valve of the root of FIGS. 1A-C after the valve has been dissected from the root and fitted and sewn into a fabric covered stent;

FIG. 2 is a sectional view taken along line 2—2 of FIG. 1B;

FIG. 3 is an elevational view of the valve-stent assembly of FIG. 1D;

DETAILED DESCRIPTION OF THE INVENTION

Figure 4A:
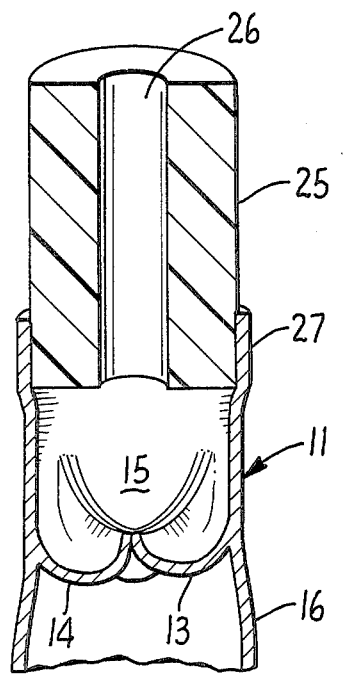
FIGS. 4A and 4B are sectional views of the aortic root of FIG. 1A placed on an adapter and initial fixation apparatus. Such placement is an alternative to packing the valve in a closed position as depicted in FIGS. 1B and 2.

The process of the invention is used to fix (tan) natural tissue cardiac valves. The valves may be mitral valves or aortic valves. Both homograft and heterograft valves may be fixed using the invention process. For aortic valve prostheses in humans, aortic porcine valves are commonly used because they are similar to human valves and easy to procure in a wide spectrum of sizes. For convenience the entire aortic root is taken. It should be procured fresh and kept in chilled saline pending fixation. It is desirable to fix the valves within about one-half hour of their procurement.

FIG. 1A shows a freshly procured porcine aortic root, generally designated 11, that includes a valve, generally designated 12. The interior of the valve 12 is comprised of three cusps or leaflets 13, 14, 15 whose bases are integral with the muscle tissue 16 that defines the aorta and whose apices extend into the aortic orifice to meet generally centrally therein. Cusps 13, 14, 15 are joined at commissures 17, 18, 19 (FIG. 2). Valve 12 is shown in its closed position in FIG. 1A.

The first step of the invention process is to partially fix valve 12 with cusps 13, 14, 15 in their closed positions. This is accomplished by contacting root 11 with a fixing agent with valve 12 maintained in its closed position. The purpose of this initial step is to substantially set the configuration of valve 12 such that the geometry and dimensions of the valve do not change significantly after this step. FIGS. 1B and 2 illustrate valve 12 during this initial step. As shown in FIGS. 1B and 2, cusps 13, 14, 15 are maintained in a closed position by packing them with three fixing agent soaked balls 22, 23, 24 of an innocuous packing material such as rayon or cotton. The material from which balls 22, 23, 24 are made is desirably capable of absorbing the fixing agent so that good contact between the cusp tissue and the fixing agent is achieved. After the cusps 13, 14, 15 are packed with balls 22, 23, 24 root 11 is submerged in the fixing agent. Aqueous solutions of glutaraldehyde, typically 0.1% to 5% by weight, may be used as the fixing agent. Other known fixing agents, such as other aldehydes, may be used in place of glutaraldehyde. Root 11 is kept submerged in the fixing agent for a time sufficient to substantially permanently set the geometry and dimensions of valve 12. Normally this will be from about one-half hour to six hours, depending on the strength of the fixing agent. Submersion in 0.5% glutaraldehyde solution for about four hours at ambient temperatures has been used with good results.

Figure 4B:
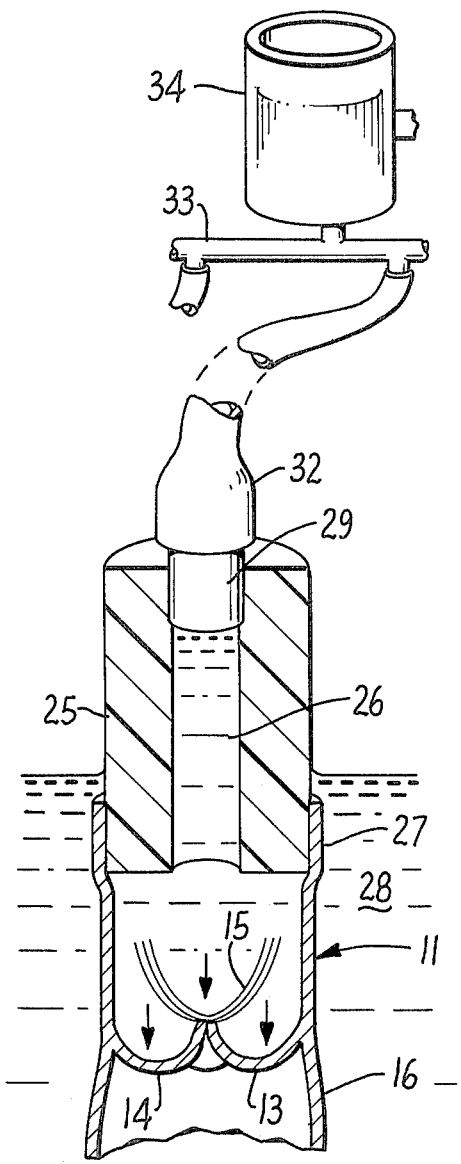

FIGS. 4A and 4B illustrate alternate and preferable means for maintaining valve 12 in a closed position during the initial fixation. The technique depicted in FIGS. 4A and 4B uses hydraulic pressure rather than packing to keep cusp 13, 14, 15 closed. A cylindrical adapter plug 25 of slightly larger diameter than the downstream orifice of root 11 and having an axial bore 26 in it is fitted snugly into the downstream end 27 of root 11. To ensure a tight fit of plug 25 in end 27, a clamp or other tightening means (not shown) may be placed around end 27, if desired. The root 11-plug 25 assembly is then submerged in a bath of fixing agent 28 and a tube 29 attached to one end of a hose 32 is fitted into the end of bore 26 distal from root 11. The other end of hose 32 is connected to a manifold 33 that in turn is connected to a tank 34 (depicted disproportionately small in FIG. 4B) filled with fixing agent 28. Hydraulic pressure (indicated by the three arrows in FIG. 4B) is thus placed on cusps 13, 14, 15, the extent of which depends on the elevation of tank 34 above the bath of fixing agent in which root 11 is submerged. Preferably about 20 mm Hg to 100 mm Hg pressure is so placed on valve 12. This amount of pressure keeps valve 12 in an expanded, closed position during the initial fixation.

After root 11 has been submerged in the fixing agent for the required time, it is removed therefrom and balls 22, 23, 24 or adapter plug 25, as the case may be, are extracted from root 11. If it is not feasible to immediately continue the processing of root 11 at this time, it may be stored in chilled saline 35 (FIG. 1C) pending such processing. It should be stored in saline 35 for as short a time as possible, preferably not more than about one-half day.

Next, root 11 is removed from saline 35 if it has been necessary to store it temporarily, and valve 12 is dissected from root 11 by trimming away excess tissue 16. The tissue should be trimmed as completely as possible, especially in the right coronary cusp muscle layer. Valve 12, after trimming, is shown in FIG. 1D. Valve 12 is then fitted to a stent, generally designated 36, and affixed thereto by sutures 37. Stent 36 is preferably of the type described in U.S. Pat. Nos. 3,983,581 and 4,035,849 and the description of the structure, composition, and manufacture of such stents is incorporated herein by reference. Stent 36 comprises a plastic frame 38, a fabric cover 39 enclosing the entire surface of frame 38, and an annular sewing ring 42 enclosed within a pocket in cover 39 near the atrial edge 43 of frame 38. It is desirable that the thickness of atrial edge 43 be about 0.025 in. It may be necessary to trim edge 43, especially at the right coronary cusp position, of frame 38 to achieve such thickness. The structural integrity of frame 38 must not be impaired by such trimming. By keeping the thickness of edge 43 as small as possible, the cross sectional area of the aortic orifice is maximized. This improves the hydraulic performance of the valve. The prosthesis appears as in FIGS. 1D and 3 after the valve 12 has been fitted and sewn into stent 36.

Figure 5:
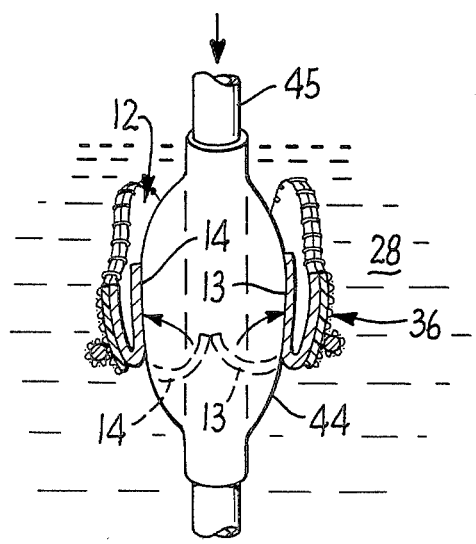
FIG. 5 is a partially sectional view of the valve-stent assembly of FIGS. 2 and 3 showing the assembly as it appears during the final fixation.

Valve 12 is next readied for the final fixation step. The apparatus used in this final step is shown in FIG. 5. It includes a section of inflatable tube 44 (an endotracheal tube cuff may be used) connected at each of its ends to rigid tubing 45. The fit between tube 44 and tube 45 should be tight so that tube 44 may be inflated. Clamping means (not shown) may be used to ensure a tight fit. This apparatus is inserted axially through valve 12 (shown unexpanded in phantom in FIG. 5), and tubing 45 is attached to a pressure source (not shown). This causes tubing 44 to expand (expanded position shown in solid in FIG. 5) and force cusps 13, 14, 15 into an open position. The forcing of cusps 13, 14, 15 is indicated by the arrows in FIG. 5. This assembly is then submerged in the bath of fixing agent 28 for a time sufficient to significantly increase the extent of fixation. Again, this time may vary depending upon the nature and strength of the fixing agent. With 0.1% to 5% glutaraldehyde it will usually take between about one-half hour and six hours to achieve the desired degree of fixation.

For valves that have undergone an initial fixation in 0.5% glutaraldehyde for four hours, it has been found that final fixation with the valve expanded in the open position in 0.5% glutaraldehyde for about four hours gives good results. The purpose of the final fixation is to predispose cusps 13, 14, 15 to an open configuration and improve their flexibility. This in turn tends to reduce the in vivo pressure gradient required to open valve 12 and may increase blood flow rate through valve 12 and reduce the pressure drop across valve 12.

Figure 6:
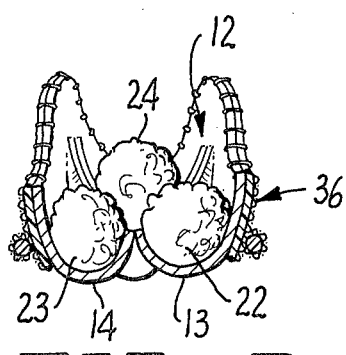
FIG. 6 is a sectional view of the valve-stent assembly of FIGS. 2 and 3 after final fixation and packed for storage until it is to be used.

After valve 12 has been submerged in fixing agent 28 for the required time, the tubing-valve assembly is removed therefrom, tube 44 is deflated by disconnecting tubing 45 from the pressure source and tubings 44 and 45 are removed from the valve. The valve may then be stored pending its implantation by packing it in the closed position with balls 22, 23, 24 (FIG. 6).

Modifications of the above described process and/or the equipment and materials used to carry it out that are obvious to those of skill in the medical, mechanical, chemical, or prosthesis arts are intended to be within the scope of the following claims.

I claim:

1. Process for fixing a natural tissue heart valve prosthesis comprising:
   (a) contacting the valve with a fixing agent with the valve cusps in a closed position so as to partially fix the valve such that the configuration and dimensions of the valve are substantially set; and
   (b) thereafter contacting the valve with the fixing agent with the valve cusps in an open position whereby the valve is further fixed and the valve cusps are predisposed to an open position.

2. The process of claim 1 wherein the valve is a porcine valve.

3. The process of claim 2 wherein the fixing agent is an aqueous solution of glutaraldehyde.

4. The process of claim 3 wherein the glutaraldehyde concentration in the solution is 0.5 % by weight.

5. The process of claim 4 wherein in step (a) the valve is contacted with the glutaraldehyde solution for about four hours and in step (b) the valve is contacted with the glutaraldehyde solution for about four hours.

6. The process of claim 1 wherein the valve is packed with a packing material to hold the valve cusps in a closed position in step (a).

7. The process of claim 1 wherein hydraulic pressure is applied to ventricular side of the valve to hold the valve cusps in a closed position in step (a).

8. The process of claim 1 wherein the valve is fitted to and affixed within a stent between steps (a) and (b).

9. The process of claim 1 wherein an expandable member is placed axially within the valve and expanded therein to hold the valve cusps in an open position in step (b).

10. Process for fixing a porcine heart valve prosthesis comprising:
(a) contacting the valve with an aqueous solution of glutaraldehyde with the valve cusps in a closed position for a time sufficient to partially fix the valve and substantially set the configuration and dimensions of the valve;
(b) fitting and affixing the valve within a stent; and
(c) contacting the valve-stent assembly with an aqueous solution of glutaraldehyde with the valve cusps in an open position for a time sufficient to further fix the valve and predispose the valve cusps to an open position.

11. The process of claim 10 wherein hydraulic pressure is applied to the ventricular side of the valve to hold the valve cusps in a closed position in step (a) and an expandable member is placed axially within the valve and expanded therein to hold the valve cusps in an open position in step (c).

* * * * *